(12) United States Patent
Cao et al.

(10) Patent No.: US 7,232,787 B2
(45) Date of Patent: Jun. 19, 2007

(54) METHOD OF SYNTHESIZING MOLECULAR SIEVES

(75) Inventors: Guang Cao, Branchburg, NJ (US); Matu J. Shah, Livingston, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 287 days.

(21) Appl. No.: 10/691,268

(22) Filed: Oct. 22, 2003

(65) Prior Publication Data

US 2004/0082466 A1    Apr. 29, 2004

Related U.S. Application Data

(62) Division of application No. 09/996,874, filed on Nov. 30, 2001, now Pat. No. 6,660,682.

(51) Int. Cl.
*B01J 27/14* (2006.01)

(52) U.S. Cl. .................. 502/214; 502/402; 502/407; 502/414

(58) Field of Classification Search ............... 502/214, 502/402, 407, 414
See application file for complete search history.

(56) References Cited

U.S. PATENT DOCUMENTS

| | | | |
|---|---|---|---|
| 4,062,905 A | 12/1977 | Chang et al. | |
| 4,079,095 A | 3/1978 | Givens et al. | |
| 4,310,440 A | 1/1982 | Wilson et al. | 252/435 |
| 4,440,871 A * | 4/1984 | Lok et al. | 502/214 |
| 4,499,327 A | 2/1985 | Kaiser | |
| 4,500,651 A | 2/1985 | Lok et al. | |
| 4,554,143 A | 11/1985 | Messina et al. | |
| 4,567,029 A | 1/1986 | Wilson et al. | |
| 4,677,242 A | 6/1987 | Kaiser | |
| 4,677,243 A | 6/1987 | Kaiser | |
| 4,680,170 A | 7/1987 | Lowe et al. | 423/703 |
| 4,752,651 A | 6/1988 | Kaiser | |
| 4,853,197 A | 8/1989 | Wilson et al. | |
| 4,873,390 A | 10/1989 | Lewis et al. | |
| 5,095,163 A | 3/1992 | Barger | |
| 5,191,141 A | 3/1993 | Barger et al. | |
| 5,367,100 A | 11/1994 | Gongwei et al. | |
| 5,714,662 A | 2/1998 | Vora et al. | |
| 6,166,282 A | 12/2000 | Miller | |

FOREIGN PATENT DOCUMENTS

| | | |
|---|---|---|
| EP | 0 065 401 | 11/1982 |
| EP | 0 463 793 A3 * | 1/1992 |
| EP | 0 463 793 | 2/1992 |

* cited by examiner

*Primary Examiner*—Robert D. Harlan
(74) *Attorney, Agent, or Firm*—David M. Weisberg

(57) ABSTRACT

The invention is directed to a method of synthesizing a molecular sieve. In particular, the invention is directed to a method for synthesizing a molecular sieve, especially a silicoaluminophosphate molecular sieve, in the presence of a templating agent and a polymeric base. The invention is also directed to formulating the molecular sieve into a catalyst useful in a process for producing olefin(s), preferably ethylene and/or propylene, from a feedstock, preferably an oxygenate containing feedstock.

10 Claims, No Drawings

METHOD OF SYNTHESIZING MOLECULAR SIEVES

RELATED APPLICATION DATA

This application is a divisional of U.S. application Ser. No. 09/996,874, filed Nov. 30, 2001, now U.S. Pat. No. 6,660,682 which is hereby incorporated by reference.

FIELD OF THE INVENTION

The present invention relates to a method of synthesizing a molecular sieve. In particular, the invention is directed to a method for synthesizing a molecular sieve, especially a silicoaluminophosphate molecular sieve, and to its formulation into a catalyst composition useful in a process for producing olefin(s), preferably ethylene and/or propylene, from a feedstock, preferably an oxygenate containing feedstock.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. Ethylene and propylene are important commodity petrochemicals useful in a variety of processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide.

The petrochemical industry has known for some time that oxygenates, especially alcohols, are convertible into light olefin(s). There are numerous technologies available for producing oxygenates including fermentation or reaction of synthesis gas derived from natural gas, petroleum liquids, carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Syngas production processes are well known, and include conventional steam reforming, autothermal reforming, or a combination thereof.

Methanol, the preferred alcohol for light olefin production, is typically synthesized from the catalytic reaction of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor. The preferred methanol conversion process is generally referred to as a methanol-to-olefin(s) process, where methanol is converted to primarily ethylene and/or propylene in the presence of a molecular sieve.

Molecular sieves are porous solids having pores of different sizes such as zeolites or zeolite-type molecular sieves, carbons and oxides. There are amorphous and crystalline molecular sieves. Molecular sieves include natural, mineral molecular sieves, or chemically formed, synthetic molecular sieves that are typically crystalline materials containing silica, and optionally alumina. The most commercially useful molecular sieves for the petroleum and petrochemical industries are known as zeolites. A zeolite is an aluminosilicate having an open framework structure that usually carries negative charges. This negative charge within portions of the framework is a result of an $Al^{3+}$ replacing a $Si^{4+}$. Cations counter-balance these negative charges preserving the electroneutrality of the framework, and these cations are exchangeable with other cations and/or protons. Synthetic molecular sieves, particularly zeolites, are typically synthesized by mixing sources of alumina and silica in a strongly basic aqueous media, often in the presence of a structure directing agent or templating agent. The structure of the molecular sieve formed is determined in part by solubility of the various sources, silica-to-alumina ratio, nature of the cation, synthesis temperature, order of addition, type of templating agent, and the like.

A zeolite is typically formed from corner sharing the oxygen atoms of $[SiO_4]$ and $[AlO_4]$ tetrahedra or octahedra. Zeolites in general have a one-, two- or three-dimensional crystalline pore structure having uniformly sized pores of molecular dimensions that selectively adsorb molecules that can enter the pores, and exclude those molecules that are too large. The pore size, pore shape, interstitial spacing or channels, composition, crystal morphology and structure are a few characteristics of molecular sieves that determine their use in various hydrocarbon adsorption and conversion processes.

There are many different types of zeolites well known to convert a feedstock, especially oxygenate containing feedstock, into one or more olefin(s). For example, U.S. Pat. No. 5,367,100 describes the use of a well known zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; and U.S. Pat. No. 4,079,095 describes the use of ZSM-34 to convert methanol to hydrocarbon products such as ethylene and propylene.

Crystalline aluminophosphates, $ALPO_4$, formed from corner sharing $[AlO_2]$ and $[PO_2]$ tetrahedra linked by shared oxygen atoms are described in U.S. Pat. No. 4,310,440 to produce light olefin(s) from an alcohol. Metal containing aluminophosphate molecular sieves, MeAPO's and ElAPO's, have been also described to convert alcohols into olefin(s). MeAPO's have a $[MeO_2]$, $[AlO_2]$ and $[PO_2]$ tetrahedra microporous structure, where Me is a metal source having one or more of the divalent elements Co, Fe, Mg, Mn and Zn, and trivalent Fe from the Periodic Table of Elements. ElAPO's have an $[ElO_2]$, $[AlO_2]$ and $[PO_2]$ tetrahedra microporous structure, where El is a metal source having one or more of the elements As, B, Be, Ga, Ge, Li, Ti and Zr. MeAPO's and ElAPO's are typically synthesized by the hydrothermal crystallization of a reaction mixture of a metal source, an aluminum source, a phosphorous source and a templating agent. The preparation of MeAPO's and ElAPO's are found in U.S. Pat. Nos. 4,310,440, 4,500,651, 4,554,143, 4,567,029, 4,752,651, 4,853,197, 4,873,390 and 5,191,141.

One of the most useful molecular sieves for converting methanol to olefin(s) are those ELAPO's or MeAPO's where the metal source is silicon, often a fumed, colloidal or precipitated silica. These molecular sieves are known as silicoaluminophosphate molecular sieves. Silicoaluminophosphate (SAPO) molecular sieves contain a three-dimensional microporous crystalline framework structure of $[SiO_2]$, $[AlO_2]$ and $[PO_2]$ corner sharing tetrahedral units. SAPO synthesis is described in U.S. Pat. No. 4,440,871, which is herein fully incorporated by reference. SAPO is generally synthesized by the hydrothermal crystallization of a reaction mixture of silicon-, aluminum- and phosphorus-sources and at least one templating agent. Synthesis of a SAPO molecular sieve, its formulation into a SAPO catalyst, and its use in converting a hydrocarbon feedstock into olefin(s), particularly where the feedstock is methanol, is shown in U.S. Pat. Nos. 4,499,327, 4,677,242, 4,677,243, 4,873,390, 5,095,163, 5,714,662 and 6,166,282, all of which are herein fully incorporated by reference.

Templating agents are used in the synthesis of molecular sieves, particularly SAPO molecular sieves, as a crystal structure-directing agent or affecting agent. Furthermore, templating agents are typically nitrogen containing organic bases such as quaternary ammonium salts or hydroxides. Typically, because templating agents are also used to control the pH during the synthesis of molecular sieves, the quaternary ammonium hydroxide is often used instead of the less expensive quaternary ammonium salt. Additionally, the quantity of the templating agent used is often dictated by the pH of the reaction mixture in which the molecular sieve forms. Templating agents are typically used in excess, relative to its incorporation in the crystalline molecular sieve product, in order to control the pH and/or alkaline content in the synthesis of molecular sieves, for example as described in U.S. Pat. No. 4,440,871.

The templating agent is oftentimes the most costly ingredient used in synthesizing molecular sieves. Using a second, less expensive base as a pH controller, in addition to a templating agent, in principle leads to a reduction in the cost of synthesizing a particular molecular sieve, provided that the pH controller does not interfere with the synthesis of the desired molecular sieve. As described in U.S. Pat. No. 4,440,871 in a SAPO molecular sieve synthesis, using an inorganic base to reduce the amount of organic templating agent, often results in the formation of undesirable dense phase products. Some organic bases, for instance, dipropylamine, have been combined with a templating agent, tetraethylammonium hydroxide, for the synthesis of a SAPO molecular sieve. Monomeric organic bases such as dipropylamine are volatile and raise various environmental and safety concerns. Additionally, higher pressure equipment is needed for the hydrothermal synthesis of molecular sieves using volatile monomeric organic bases.

Therefore, it would be desirable to have an improved method for reducing the amount of templating agent utilized in synthesizing a molecular sieve.

SUMMARY OF THE INVENTION

This invention provides a method of synthesizing a molecular sieve, to its formulation into a molecular sieve catalyst composition, and to it use in a process, preferably a conversion process, for making one or more olefin(s), particularly light olefin(s).

In one embodiment the invention is directed to a method for synthesizing a molecular sieve utilizing a templating agent, preferably an organic templating agent, and a polymeric base. In preferred embodiments, the polymeric base is a polymeric base, or a soluble and/or non-volatile polymeric base or a non-ionic polymeric base, or a combination thereof, and most preferably the polymeric base is a polymeric imine, preferably a polyethylene imine or polyethylenimine.

In another embodiment the invention relates to a method for synthesizing a molecular sieve, the method comprising the steps of: (a) forming a reaction mixture of at least one templating agent and at least one of the group consisting of a silicon source, a phosphorous source and an aluminum source; (b) introducing to the reaction mixture a non-ionic polymeric base or a soluble polymeric base; and (c) removing the molecular sieve from the reaction mixture. In one preferred embodiment, the polymeric base is non-volatile and/or has a pH of from about 8 to about 14 in an aqueous solution, and/or has an average molecular weight $M_w$ greater than 500. In another preferred embodiment of this embodiment, the polymeric base is a polymeric imine.

In the most preferred embodiment the invention relates to a method of synthesizing a molecular sieve, the method comprising the steps of: (a) combining a silicon source, an aluminum source, and/or a phosphorous source; (b) introducing an organic templating agent; (c) introducing a polymeric base; and (d) removing the molecular sieve. In a preferred embodiment, the mole ratio of the organic templating agent to the monomeric unit of the polymeric base is from about 0.01 to 1, preferably from 0.1 to 0.75, and more preferably 0.25 to 0.5.

In another embodiment of the invention the molecular sieve described above is formulated into a molecular sieve catalyst composition. In this embodiment, the molecular sieve removed from step (c) above and step (d) immediately above is combined with a matrix material and optionally a binder to form the molecular sieve catalyst composition of the invention.

In yet another embodiment, the invention is directed to a process for producing olefin(s) in the presence of any of the above molecular sieves and catalyst compositions thereof. In particular, the process involves producing olefin(s) in a process for converting a feedstock, preferably a feedstock containing an oxygenate, more preferably a feedstock containing an alcohol, and most preferably a feedstock containing methanol.

DETAILED DESCRIPTION OF THE INVENTION

Introduction

The invention is directed toward a method for synthesizing a molecular sieve using a templating agent and a polymeric base. It has been found that a polymeric base is useful in combination with a decreased amount of templating agent to produce a given molecular sieve. Also, it has been found that the use of a salt as a templating agent, such as a quaternary ammonium salt, rather than the more expensive quaternary ammonium hydroxide, is useful in combination with a polymeric base to synthesize a molecular sieve. Without being bound to any particular theory, it is believed that the soluble or neutral polymeric base, especially a polymeric imine, more specifically a polyethylenimine, is useful to control pH, and therefore, less amount of a basic organic templating agent, or even a non-basic organic templating agent can be used to synthesize a particular molecular sieve.

Molecular Sieves and Catalysts Thereof

Molecular sieves have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite*

*Framework Types*, 5th edition, Elsevier, London, England (2001), which is herein fully incorporated by reference.

Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1-67, Elsevier Science, B. V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, $SAPO_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as $[MeO_2]$, and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

Molecular Sieve Synthesis

The synthesis of molecular sieves is described in many of the references discussed above. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In a preferred embodiment the molecular sieves are synthesized by forming a reaction product of a source of silicon, a source of aluminum, a source of phosphorous, an organic templating agent, preferably a nitrogen containing organic templating agent, and one or more polymeric bases. This particularly preferred embodiment results in the synthesis of a silicoaluminophosphate crystalline material that is then isolated by filtration, centrifugation and/or decanting.

Non-limiting examples of silicon sources include a silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $ALPO_4$, phosphorous salts, or combinations thereof. The preferred source of phosphorous is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium including salts thereof, and tetrabutylammonium including salts thereof, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N', N',N,N-tetramethyl-(1,6) hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butylamine, ethylenediamine, pyrrolidine, and 2-imidazolidone.

The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. The most preferred templating agent is tetraethyl ammonium hydroxide and salts thereof, particularly when producing a silicoaluminophosphate molecular sieve. In one embodiment, a combination of two or more of any of the above templating agents is used in combination with one or more of a silicon-, aluminum-, and phosphorous-source, and a polymeric base.

Polymeric bases, especially polymeric bases that are soluble or non-ionic, useful in the invention, are those having a pH sufficient to control the pH desired for synthesizing a given molecular sieve, especially a SAPO molecular sieve. In a preferred embodiment, the polymeric base is soluble or the polymeric base is non-ionic, preferably the polymeric base is a non-ionic and soluble polymeric base, and most preferably the polymeric base is a polymeric imine. In one embodiment, the polymeric base of the invention has a pH in an aqueous solution, preferably water, from greater than 7 to about 14, more preferably from about 8 to about 14, most preferably from about 9 to 14.

In another embodiment, the non-volatile polymeric base is represented by the formula: $(R-NH)_x$, where (R-NH) is a polymeric or monomeric unit where R contains from 1 to 20 carbon atoms, preferably from 1 to 10 carbon atoms, more preferably from 1 to 6 carbon atoms, and most preferably from 1 to 4 carbon atoms; x is an integer from 1 to 500,000. In one embodiment, R is a linear, branched, or cyclic polymer, monomeric, chain, preferably a linear polymer chain having from 1 to 20 carbon atoms.

In another embodiment, the polymeric base is a water miscible polymeric base, preferably in an aqueous solution. In yet another embodiment, the polymeric base is a polyethylenimine that is represented by the following general formula:

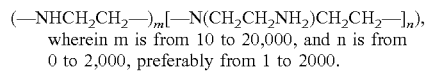
wherein m is from 10 to 20,000, and n is from 0 to 2,000, preferably from 1 to 2000.

In another embodiment, the polymeric base of the invention has a average molecular weight from about 500 to about 1,000,000, preferably from about 2,000 to about 800,000, more preferably from about 10,000 to about 750,000, and most preferably from about 50,000 to about 750,000.

In another embodiment, the mole ratio of the monomeric unit of the polymeric base of the invention, containing one basic group, to the templating agent(s) is less than 20, preferably less than 12, more preferably less than 10, even more preferably less than 8, still even more preferably less than 5, and most preferably less than 4.

Non-limiting examples of polymer bases include: epichlorohydrin modified polyethylenimine, ethoxylated polyethylenimine, polypropylenimine diamine dendrimers (DAB-Am-n), poly(allylamine) $[CH_2CH(CH_2NH_2)]_n$, poly(1,2-dihydro-2,2,4-trimethylquinoline), and poly(dimethylamine-co-epichlorohydrin-co-ethylenediamine).

In another embodiment the invention is directed to a method for synthesizing a molecular sieve utilizing a templating agent, preferably an organic templating agent such as an organic amine, an ammonium salt and/or an ammonium hydroxide, in combination with a polymeric base such as polyethylenimine.

In a typical synthesis of the molecular sieve, the phosphorous-, aluminum-, and/or silicon-containing components are mixed, preferably while stirring and/or agitation and/or seeding with a crystalline material, optionally with an alkali metal, in a solvent such as water, and one or more templating agents and a polymeric base, to form a synthesis mixture that is then heated under crystallization conditions of pressure and temperature as described in U.S. Pat. Nos. 4,440,871, 4,861,743, 5,096,684, and 5,126,308, which are all herein fully incorporated by reference. The polymeric base is combined with the at least one templating agent, and one or more of the aluminum source, phosphorous source, and silicon source, in any order, for example, simultaneously with one or more of the sources, premixed with one or more of the sources and/or templating agent, after combining the sources and the templating agent, and the like.

Generally, the synthesis mixture described above is sealed in a vessel and heated, preferably under autogenous pressure, to a temperature in the range of from about 80° C. to about 250° C., preferably from about 100° C. to about 250° C., more preferably from about 125° C. to about 225° C., even more preferably from about 150° C. to about 180° C. In another embodiment, the hydrothermal crystallization temperature is less than 225° C., preferably less than 200° C. to about 80° C., and more preferably less than 195° C. to about 100° C.

In yet another embodiment, the crystallization temperature is increased gradually or stepwise during synthesis, preferably the crystallization temperature is maintained constant, for a period of time effective to form a crystalline product. The time required to form the crystalline product is typically from immediately up to several weeks, the duration of which is usually dependent on the temperature; the higher the temperature the shorter the duration. In one embodiment, the crystalline product is formed under heating from about 30 minutes to around 2 weeks, preferably from about 45 minutes to about 240 hours, and more preferably from about 1 hour to about 120 hours.

In one embodiment, the synthesis of a molecular sieve is aided by seeds from another or the same framework type molecular sieve.

The hydrothermal crystallization is carried out with or without agitation or stirring, for example stirring or tumbling. The stirring or agitation during the crystallization period may be continuous or intermittent, preferably continuous agitation. Typically, the crystalline molecular sieve product is formed, usually in a slurry state, and is recovered by any standard technique well known in the art, for example centrifugation or filtration. The isolated or separated crystalline product, in an embodiment, is washed, typically, using a liquid such as water, from one to many times. The washed crystalline product is then optionally dried, preferably in air.

One method for crystallization involves subjecting an aqueous reaction mixture containing an excess amount of a templating agent and polymeric base, subjecting the mixture to crystallization under hydrothermal conditions, establishing an equilibrium between molecular sieve formation and dissolution, and then, removing some of the excess templating agent and/or organic base to inhibit dissolution of the molecular sieve. See for example U.S. Pat. No. 5,296,208, which is herein fully incorporated by reference.

Another method of crystallization is directed to not stirring a reaction mixture, for example a reaction mixture containing at a minimum, a silicon-, an aluminum-, and/or a phosphorous-composition, with a templating agent and a polymeric base, for a period of time during crystallization. See PCT WO 01/47810 published Jul. 5, 2001, which is herein fully incorporated by reference.

Other methods for synthesizing molecular sieves or modifying molecular sieves are described in U.S. Pat. No. 5,879,655 (controlling the ratio of the templating agent to phosphorous), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorous modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. patent application Ser. No. 09/929,949 filed Aug. 15, 2001 (cooling molecular sieve), U.S. patent application Ser. No. 09/615,526 filed Jul. 13, 2000 (metal impregnation including copper), U.S. patent application Ser. No. 09/672,469 filed Sep. 28, 2000 (conductive microfilter), and U.S. patent application Ser. No. 09/754,812 filed Jan. 4, 2001 (freeze drying the molecular sieve), which are all herein fully incorporated by reference.

In one preferred embodiment, when a templating agent is used in the synthesis of a molecular sieve, it is preferred that the templating agent is substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent.

Molecular sieve have either a high silicon (Si) to aluminum (Al) ratio or a low silicon to aluminum ratio, however, a low Si/Al ratio is preferred for SAPO synthesis. In one embodiment, the molecular sieve has a Si/Al ratio less than 0.65, preferably less than 0.40, more preferably less than 0.32, and most preferably less than 0.20. In another embodiment the molecular sieve has a Si/Al ratio in the range of from about 0.65 to about 0.10, preferably from about 0.40 to about 0.10, more preferably from about 0.32 to about 0.10, and more preferably from about 0.32 to about 0.15.

The pH of a reaction mixture containing at a minimum a silicon-, aluminum-, and/or phosphorous-composition, a templating agent, and a polymeric base should be in the range of from 2 to 10, preferably in the range of from 4 to 9, and most preferably in the range of from 5 to 8. The pH can be controlled by the addition of basic or acidic compounds as necessary to maintain the pH during the synthesis in the preferred range of from 4 to 9. In another embodiment, the templating agent and/or polymeric base is added to the reaction mixture of the silicon source and phosphorous source such that the pH of the reaction mixture does not exceed 10.

In one embodiment, the molecular sieves of the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

Method for Making Molecular Sieve Catalyst Compositions

Once the molecular sieve is synthesized, depending on the requirements of the particular conversion process, the molecular sieve is then formulated into a molecular sieve catalyst composition, particularly for commercial use. The molecular sieves synthesized above are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by well-known techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105-144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve synthesized above, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 μm to about 0.6 μm with a D90 particle size distribution of less than about 1 μm.

In one embodiment, the binder, the molecular sieve and the matrix material are combined in the presence of a liquid to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

Upon combining the molecular sieve and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve and matrix material, and the optional binder, are in the same or different liquid, and are combined in any order, together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 μm to about 300 μm, preferably from about 50 μm to about 250 μm, more preferably from about 50 μm to about 200 μm, and most preferably from about 65 μm to about 90 μm.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve in powder form.

Generally, the size of the powder is controlled to some extent by the solids content of the slurry. However, control of the size of the catalyst composition and its spherical characteristics are controllable by varying the slurry feed properties and conditions of atomization.

Other methods for forming a molecular sieve catalyst composition is described in U.S. patent application Ser. No. 09/617,714 filed Jul. 17, 2000 (spray drying using a recycled molecular sieve catalyst composition), which is herein incorporated by reference.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature ranges from about 15 minutes to about 2 hours.

In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

Other methods for activating a molecular sieve catalyst composition, in particular where the molecular sieve is a reaction product of the combination of a silicon-, phosphorous-, and aluminum-sources, a templating agent, and a polymeric base, more particularly a silicoaluminophosphate catalyst composition (SAPO) are described in, for example, U.S. Pat. No. 5,185,310 (heating molecular sieve of gel alumina and water to 450° C.), PCT WO 00/75072 published Dec. 14, 2000 (heating to leave an amount of template), and U.S. application Ser. No. 09/558,774 filed Apr. 26, 2000 (rejuvenation of molecular sieve), which are all herein fully incorporated by reference.

Process For Using the Molecular Sieve Catalyst Compositions

The molecular sieve catalysts and compositions described above are useful in a variety of processes including: cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene, polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumeme or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

Preferred processes are conversion processes including: naphtha to highly aromatic mixtures; light olefin(s) to gasoline, distillates and lubricants; oxygenates to olefin(s); light paraffins to olefins and/or aromatics; and unsaturated hydrocarbons (ethylene and/or acetylene) to aldehydes for conversion into alcohols, acids and esters. The most preferred process of the invention is a process directed to the conversion of a feedstock comprising one or more oxygenates to one or more olefin(s).

The molecular sieve catalyst compositions described above are particularly useful in conversion processes of different feedstock. Typically, the feedstock contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene an/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The are many processes used to convert feedstock into olefin(s) including various cracking processes such as steam cracking, thermal regenerative cracking, fluidized bed cracking, fluid catalytic cracking, deep catalytic cracking, and visbreaking.

The most preferred process is generally referred to as gas-to-olefins (GTO) or alternatively, methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent. In another embodiment of the process for conversion of one or more oxygenates to one or more olefin(s), the amount of ethylene and/or propylene produced based on the total weight of hydrocarbon product produced is greater than 65 weight percent, preferably greater than 70 weight percent, more preferably greater than 75 weight percent, and most preferably greater than 78 weight percent.

In another embodiment of the process for conversion of one or more oxygenates to one or more olefin(s), the amount ethylene produced in weight percent based on the total weight of hydrocarbon product produced, is greater than 30 weight percent, more preferably greater than 35 weight percent, and most preferably greater than 40 weight percent. In yet another embodiment of the process for conversion of one or more oxygenates to one or more olefin(s), the amount of propylene produced in weight percent based on the total weight of hydrocarbon product produced is greater than 20 weight percent, preferably greater than 25 weight percent, more preferably greater than 30 weight percent, and most preferably greater than 35 weight percent.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the processes for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is a Group IIIA or VIII element from the Periodic Table of Elements) molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, preferably after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

By controlling the flow of the regenerated molecular sieve catalyst composition or cooled regenerated molecular sieve catalyst composition from the regeneration system to the reactor system, the optimum level of coke on the molecular sieve catalyst composition entering the reactor is maintained. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336-337), which is herein incorporated by reference.

Coke levels on the molecular sieve catalyst composition is measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one preferred embodiment, the mixture of fresh molecular sieve catalyst composition and regenerated molecular sieve catalyst composition and/or cooled regenerated molecular sieve catalyst composition contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a dethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat.

Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249-271 and 894-899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent gas withdrawn from the reactor or converting those products produced as a result of the recovery system utilized.

In one embodiment, the effluent gas withdrawn from the reactor is passed through a recovery system producing one or more hydrocarbon containing stream(s), in particular, a three or more carbon atom ($C_3^+$) hydrocarbon containing stream. In this embodiment, the $C_3^+$ hydrocarbon containing stream is passed through a first fractionation zone producing a crude $C_3$ hydrocarbon and a $C_4^+$ hydrocarbon containing stream, the $C_4^+$ hydrocarbon containing stream is passed through a second fractionation zone producing a crude $C_4$ hydrocarbon and a $C_5^+$ hydrocarbon containing stream. The four or more carbon hydrocarbons include butenes such as butene-1 and butene-2, butadienes, saturated butanes, and isobutanes.

The effluent gas removed from a conversion process, particularly a MTO process, typically has a minor amount of hydrocarbons having 4 or more carbon atoms. The amount of hydrocarbons having 4 or more carbon atoms is typically in an amount less than 20 weight percent, preferably less than 10 weight percent, more preferably less than 5 weight percent, and most preferably less than 2 weight percent, based on the total weight of the effluent gas withdrawn from a MTO process, excluding water. In particular with a conversion process of oxygenates into olefin(s) utilizing a molecular sieve catalyst composition the resulting effluent gas typically comprises a majority of ethylene and/or propylene and a minor amount of four carbon and higher carbon number products and other byproducts, excluding water.

Suitable well known reaction systems as part of the recovery system primarily take lower value products and convert them to higher value products. For example, the $C_4$ hydrocarbons, butene-1 and butene-2 are used to make alcohols having 8 to 13 carbon atoms, and other specialty chemicals, isobutylene is used to make a gasoline additive, methyl-t-butylether, butadiene in a selective hydrogenation unit is converted into butene-1 and butene-2, and butane is useful as a fuel.

Non-limiting examples of reaction systems include U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams*, Pet. & Coal, Vol. 37, No. 4 (1995) (dimerizing or oligomerizing propylene, butylene and pentylene), which are all herein fully incorporated by reference.

The preferred light olefin(s) produced by any one of the processes described above, preferably conversion processes, are high purity prime olefin(s) products that contains a single carbon number olefin in an amount greater than 80 percent, preferably greater than 90 weight percent, more preferably greater than 95 weight percent, and most preferably no less than about 99 weight percent, based on the total weight of the olefin.

In one embodiment, high purity prime olefin(s) are produced in the process of the invention at rate of greater than 5 kg per day, preferably greater than 10 kg per day, more preferably greater than 20 kg per day, and most preferably greater than 50 kg per day. In another embodiment, high purity ethylene and/or high purity propylene is produced by the process of the invention at a rate greater than 4,500 kg per day, preferably greater than 100,000 kg per day, more preferably greater than 500,000 kg per day, even more preferably greater than 1,000,000 kg per day, yet even more preferably greater than 1,500,000 kg per day, still even more preferably greater than 2,000,000 kg per day, and most preferably greater than 2,500,000 kg per day.

Other conversion processes, in particular, a conversion process of an oxygenate to one or more olefin(s) in the presence of a molecular sieve catalyst composition, especially where the molecular sieve is synthesized from a silicon-, phosphorous-, and alumina-source, include those described in for example: U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in effluent gas fed to another reactor) PCT WO 01/60770 published Aug. 23, 2001 and U.S. patent application Ser. No. 09/627,634 filed Jul. 28, 2000 (high pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas.

Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through a well known purification processes, distillation, separation and fractionation, resulting in a purified oxygenate containing stream, for example, commercial Grade A and AA methanol.

The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process is described in EP-B-0 933 345, which is herein fully incorporated by reference.

In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. Polymerization processes include those non-limiting examples described in the following: U.S. Pat. Nos. 4,543,399, 4,588,790, 5,028,670, 5,317,036, 5,352,749, 5,405,922, 5,436,304, 5,453,471, 5,462,999, 5,616,661, 5,627,242, 5,665,818, 5,677,375, 5,668,228, 5,712,352 and 5,763,543 and EP-A-0 794 200, EP-A-0 802 202, EP-A2-0 891 990 and EP-B-0 634 421 describe gas phase polymerization processes; U.S. Pat. Nos. 3,248,179 and 4,613,484, 6,204,344, 6,239,235 and 6,281, 300 describe slurry phase polymerization processes; U.S. Pat. Nos. 4,271,060, 5,001,205, 5,236,998 and 5,589,555 describe solution phase polymerization processes; and U.S. Pat. Nos. 3,917,577, 4,175,169, 4,935,397, and 6,127,497 describe high pressure polymerization processes; all of which are herein fully incorporated by reference.

These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. Non-limiting examples of polymerization catalysts are described in U.S. Pat. Nos. 3,258,455, 3,305,538, 3,364,190, 3,645,992, 4,076,698, 4,115,639, 4,077,904 4,482,687, 4,564,605, 4,659,685, 4,721,763, 4,879,359, 4,960,741, 4,302,565, 4,302,566, 4,302,565, 4,302,566, 4,124,532, 4,302,565, 5,763,723, 4,871,705, 5,120,867, 5,324,800, 5,347,025, 5,384,299, 5,391,790, 5,408,017, 5,491,207, 5,455,366, 5,534,473, 5,539,124, 5,554,775, 5,621,126, 5,684,098, 5,693,730, 5,698,634, 5,710,297, 5,714,427, 5,728,641, 5,728,839, 5,753,577, 5,767,209, 5,770,753 and 5,770,664, 5,527,752, 5,747,406, 5,851,945 and 5,852,146, all of which are herein fully incorporated by reference.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a zeolite or zeolite-type molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

Polymerization conditions vary depending on the polymerization process, polymerization catalyst system and the polyolefin produced. Typical conditions of polymerization pressure vary from about 100 psig (690 kPag) to greater than about 1000 psig (3448 kPag), preferably in the range of from about 200 psig (1379 kPag) to about 500 psig (3448 kPag), and more preferably in the range of from about 250 psig (1724 kPag) to about 350 psig (2414 kPag). Typical conditions of polymerization temperature vary from about 0° C. to about 500° C., preferably from about 30° C. to about 350° C., more preferably in the range of from about 60° C. to 250° C., and most preferably in the range of from about 70° C. to about 150° C. In the preferred polymerization process the amount of polymer being produced per hour is greater than 25,000 lbs/hr (11,300 Kg/hr), preferably greater than 35,000 lbs/hr (15,900 Kg/hr), more preferably greater than 50,000 lbs/hr (22,700 Kg/hr) and most preferably greater than 75,000 lbs/hr (29,000 Kg/hr).

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

Typical ethylene based polymers have a density in the range of from 0.86 g/cc to 0.97 g/cc, a weight average molecular weight to number average molecular weight ($M_w/M_n$) of greater than 1.5 to about 10 as measured by gel permeation chromatography, a melt index ($I_2$) as measured by ASTM-D-1238-E in the range from 0.01 dg/min to 1000 dg/min, a melt index ratio ($I_{21}/I_2$) ($I_{21}$ is measured by ASTM-D-1238-F) of from 10 to less than 25, alternatively a $I_{21}/I_2$ of from greater than 25, more preferably greater than 40.

Polymers produced by the polymerization process are useful in such forming operations as film, sheet, and fiber extrusion and co-extrusion as well as blow molding, injection molding and rotary molding; films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications; fibers include melt spinning, solution spinning and melt blown fiber operations for use in woven or non-woven form to make filters, diaper fabrics, medical garments, geotextiles, etc; extruded articles include medical tubing, wire and cable coatings, geomembranes, and pond liners; and molded articles include single and multi-layered constructions in the form of bottles, tanks, large hollow articles, rigid food containers and toys, etc.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

EXAMPLES

In order to provide a better understanding of the present invention including representative advantages thereof, the following examples are offered.

Comparative Example 1

Preparation of Molecular Sieve Two Mole TEAOH Per Mole of $P_2O_5$

Following a typical SAPO-34 synthesis, the a silicon source, a phosphorous source and an aluminum source and a templating agent were mixed according to the following molar ratio:

2.0TEAOH:1.0$Al_2O_3$:0.3$SiO_2$:1.0$P_2O_5$:50$H_2O$ to form a reaction mixture. The sources of the ingredients were pseudo-boehmite (an aluminum source), 85% phosphoric acid (a phosphorous source), LUDOX HS-40 (a silicon source), and 40% aqueous solution of TEAOH (an organic templating agent). The order of mixing was first adding $H_3PO_4$, then $H_2O$, followed by Ludox, then Pseudo-boehmite, and finally TEAOH in the molar proportions described above. The reaction mixture was then blended into a uniform gel using a microhomogenizer. The gel was then placed into a Parr bomb with a Teflon liner, and was heated to 180° C. for six days. The solid product formed was centrifuged and washed several times with deionized water, and was then dried in a 60° C. vacuum oven overnight. The XRD, X-ray powder pattern, of the product confirms that the product is a pure SAPO-34 and having an elemental analysis of the following molar composition: $Al_{1.0}Si_{0.173}P_{0.834}$.

Example 2

Preparation of Molecular Sieve Using Polyethylenimine (PEI) Replacing Some TEAOH Polyethylenimine (available from Aldrich Chemical Company, Inc., Milwaukee, Wis.) described as ($-NHCH_2CH_2-$)$_x$[$-N(CH_2CH_2NH_2)CH_2CH_2-$]$_y$,) in a 50 weight percent (wt %) aqueous solution, and having average molecular weight ($M_w$) of 750,000, was diluted with water to a 25 wt % solution. The sources of phosphorous, silicon, aluminum, polymeric base, and templating agent were added according to the following order: first the phosphorous source, $H_3PO_4$, then $H_2O$, then the silicon source, Ludox, followed by the aluminum source, pseudo-boehmite, then the polymeric base, PEI, and lastly the templating agent, TEAOH. The reaction mixture was blended using a microhomogenizer. When higher amount of the polymeric base, PEI, was used, the gel had the consistency of a soft gum coexisting with a clear liquid. The molar ratios of ingredients for three preparations were as follows:

(1) 2.0 PEI monomeric unit ($CH_2CH_2NH$):1.5TEAOH: 1.0$Al_2O_3$:0.3$SiO_2$:1.0$P_2O_5$:50$H_2O$ (2) 4.0 PEI monomeric unit ($CH_2CH_2NH$):1.0TEAOH: 1.0$Al_2O_3$:0.3$SiO_2$:1.0$P_2O_5$:50$H_2O$ (3) 6.0 PEI monomeric unit ($CH_2CH_2NH$):0.5TEAOH: 1.0$Al_2O_3$:0.3$SiO_2$:1.0$P_2O_5$:50$H_2O$ Each reaction mixture, individually, were sealed in a Teflon lined Parr bomb and were heated to 180° C. for seven days. The solid product formed were centrifuged and washed several times with deionized water, and then dried in a 60° C. vacuum oven. The X-ray powder diffraction patterns of the three molecular sieves synthesized, preparations 1 and 2 produced pure a SAPO-34 phase, while preparation 3 produced a SAPO-34 molecular sieve plus an unidentified phase having two broad peaks at around 15 Å and 7.5 Å d-spacings.

Example 3

Preparation of a Molecular Sieve With One Mole Equivalent of Polyethylenimine (PEI) Replacing One Mole of TEAOH.

The same procedure as described in Example 1 was used except the mole ratio of the sources of silicon, aluminum, and phosphorous, the templating agent, and polymeric base, were as follows:

(4) 1.0 PEI Monomeric Unit ($CH_2CH_2NH$):1.0TEAOH: 1.0$Al_2O_3$:0.3$SiO_2$:1.0$P_2O_5$:50$H_2O$ The reaction mixture was homogenized, sealed in a Teflon lined Parr bomb and then heated to 180° C. (hydrothermal reaction temperature) for thirteen days. The solid product formed was centrifuged and washed several times with deionized water, and was dried in a 60° C. vacuum oven. The X-ray powder diffraction pattern indicated pure SAPO-34 was obtained. The SAPO-34 yield was 17.5 wt %, based on the total weight of the starting materials. Elemental analysis showed: Al, 16.5%; Si, 2.76%; P, 16.0% corresponding to the composition: $Al_{1.0}Si_{0.161}P_{0.845}$.

Example 4

Preparation of Molecular Sieve Using One Mole Equivalent of Polyethylenimine (PEI) Replacing One Mole of TEAOH, at 200° C.

The same synthesis procedure as described in Example 3 above was used except that the hydrothermal reaction temperature was set at 200° C. Crystallization proceeded for 5 days. The XRD of the molecular sieve product showed a highly crystalline SAPO-34 with a minor amount of an unidentified crystalline impurity. The molecular sieve solid yield was 17.0 wt %, based on the total weight of the starting materials. This Example 4 illustrates that crystallization time is dramatically reduced by increasing the hydrothermal synthesis reaction temperature.

Example 5

Preparation of Molecular Sieve Using Three Mole Equivalent of Polyethylenimine (PEI) and One Mole of N,N,N-trimethyladamantylammonium iodide, at 180° C.

2.07 g $H_3PO_4$(75%), 3.17 g $H_2O$, 1.08 g pseudo-boehmite, 0.16 g fumed silica, 4.03 g polyethylenimine (PEI), and 2.50 g N,N,N-trimethyladamantylammonium iodide was added, in sequence with vigorous blending. The molar ratios of the ingredients are the following: (5) 3.0 ($CH_2CH_2NH$):1.0$R^+I^-$:1.0$Al_2O_3$:0.3$SiO_2$:1.0$P_2O_5$:50$H_2O$, where $R^+I^-$ is N,N,N-trimethyladamantylammonium iodide.

In one embodiment, a molecular sieve, most preferably a SAPO molecular sieve, even more particularly a SAPO-34 molecular sieve, is formed using the templating agent, N,N,N-trimethyladamantylammonium iodide. The mixture was sealed, and crystallization carried out, as described above in Example 4. After 4 days of crystallization the crystalline molecular sieve was isolated by centrifugation and was washed with deionized water. The XRD of the solid product indicated that pure SAPO-34 (CHA structure-type) was obtained. The molecular sieve solid yield was 19.3 wt % based on the total weight of the starting materials. This example illustrates the use of a quaternary ammonium iodide salt as the templating agent, instead of the more expensive quaternary ammonium hydroxide, when a polymeric base is used to control the pH.

While the present invention has been described and illustrated by reference to particular embodiments, those of ordinary skill in the art will appreciate that the invention lends itself to variations not necessarily illustrated herein. For example, it is contemplated that the molecular sieve catalyst composition is useful in the inter-conversion of olefin(s), oxygenate to gasoline conversions reactions, malaeic anhydride, phthalic anyhdride and acrylonitrile formulation, vapor phase methanol synthesis, and various Fischer Tropsch reactions. It is further contemplated that a plug flow, fixed bed or fluidized bed process are used in combination, particularly in different reaction zones within a single or multiple reactor system. It is also contemplated the molecular sieves described herein are useful as absorbents, adsorbents, gas separators, detergents, water purifiers, and other various uses such as agriculture and horticulture. For this reason, then, reference should be made solely to the appended claims for purposes of determining the true scope of the present invention.

We claim:

1. A molecular sieve catalyst composition comprising a molecular sieve, which molecular sieve comprises, in combination, at least one templating agent, a polymeric base, and at least one of the group consisting of a silicon source, a phosphorous source and an aluminum source, said molecular sieve being synthesized by the steps of (a) forming a reaction mixture of said at least one templating agent and said at least one of the group consisting of a silicon source, a phosphorous source and an aluminum source; (b) introducing to said reaction mixture said polymeric base; and (c) removing said molecular sieve from said reaction mixture.

2. The molecular sieve catalyst composition of claim 1, wherein the molecular sieve catalyst composition is dried.

3. The molecular sieve catalyst composition of claim 1 wherein the molecular sieve catalyst composition comprises of a silicon source, a phosphorous source and an aluminum source.

4. The composition of claim 1 wherein the polymeric base is a soluble polymeric base.

5. The composition of claim 1 wherein the polymeric base is a polymeric imine.

6. The composition of claim 1 wherein the polymeric base is represented by the formula:
($-NHCH_2\ CH_2-$)$_m$ [$-N(CH_2\ CH_2\ NH_{2)CH2}\ CH_2-$]$_n$, wherein in is from 10 to 20,000, and n is from 1 to 2,000.

7. The composition of claim 1 wherein the mole ratio of the monomeric unit of the polymeric base to the remplating agent is less than 20.

8. The composition of claim 1 wherein the non-ionic polymeric base in an aqueous solution has a pH in the range of from 8 to 14.

9. The composition of claim 1 wherein the templating agent is a quaternary ammonium hydroxide or a quaternary ammonium salt.

10. The composition of claim 1 wherein the polymeric base is selected from the group consisting of: epichlorohydrin modified polyethylenimine, ethoxylated polyethylenimine, polypropylene diamine dendrimers, poly(allylamine), poly(1,2-dihydro-2,2,4-trimethylquinoline), and poly(dimethylamine-co-epichlorohydrin-co-ethylenediamine).

* * * * *